June 1, 1965 A. P. HOWARD Plant Pat. 2,522
ROSE PLANT
Filed Nov. 4, 1963
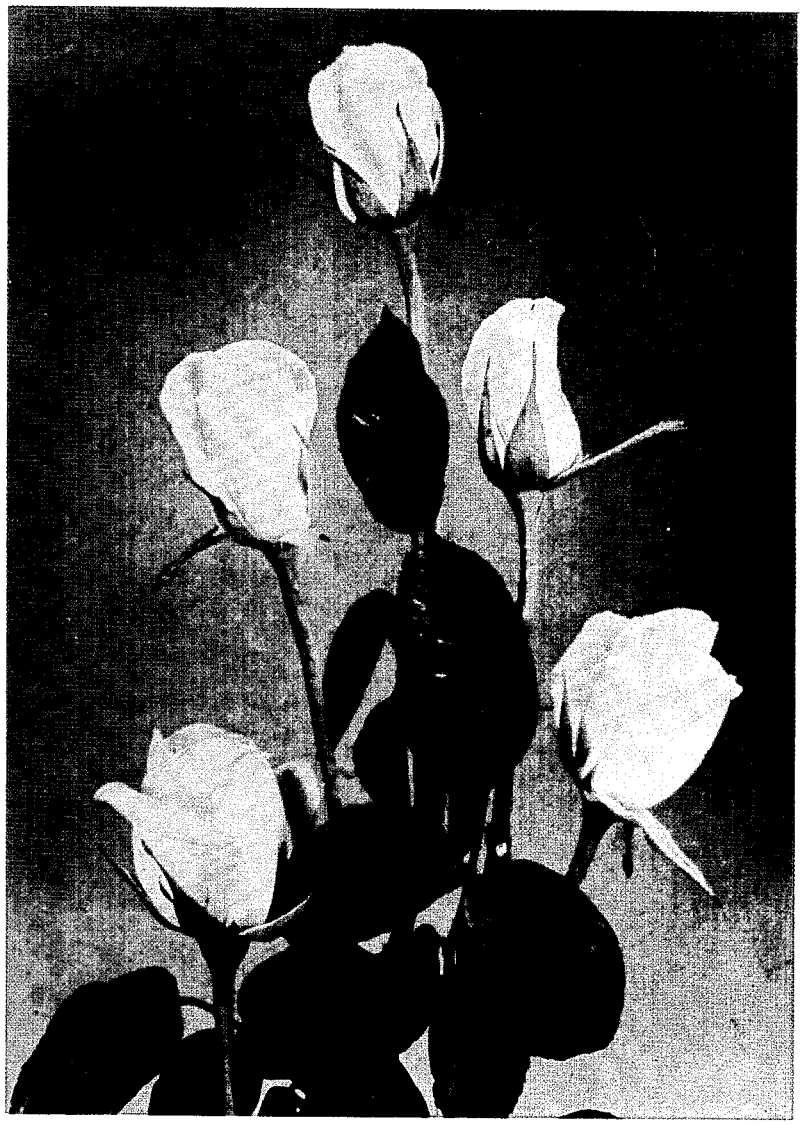
INVENTOR
ARTHUR P. HOWARD
BY J. F. Cuneo
ATTORNEY United States Patent Office Plant Pat. 2,522
Patented June 1, 1965

2,522
ROSE PLANT

Arthur P. Howard, Sierra Madre, Calif., assignor to Great Western Rose Company, Inc., Pomona, Calif., a corporation of California Filed Nov. 4, 1963, Ser. No. 327,859
1 Claim. (Cl. Plt.—14)

This invention relates to a new and distinct variety of rose plant which is ordinarily classified as a hybrid tea rose.

The plant resulted from the cross-breeding of Blanche Mallerin, a patented variety, United States Patent No. 594, and Joseph Hill, an unpatented variety, after numerous experiments conducted by me in Montebello, county of Los Angeles, State of California. The original plant was produced by me in 1956, the seed parent was Blanche Mallerin and the pollen parent was Joseph Hill.

The flowers that are produced by the new variety of rose plant are unique in that they are pure white when mature, from compact buds, have exceptionally long stems and are produced in abundance during the growing season that normally extends from the beginning of April to the end of November.

In comparing the blooms of my new variety with those of its seed parent Blanche Mallerin, the flowers are found to be pure white and better shaped, the plant is very hardy and has an upright growth with the plants reaching up to six feet in height. Compared to its pollen parent Joseph Hill, the flowers are white where those borne by Joseph Hill are yellow, the flowers hold up better when cut and the plant is considerably taller as indicated above.

The new rose belongs to the outdoor bush type and is used principally for cut flowers and garden ornamentation. The plant has been reproduced asexually by budding performed at Montebello, California. The plant and flowers reproduce true with all their distinguishing characteristics, and these distinguishing features are transmitted through succeeding propagations of the variety. The plant will not reproduce true from seed.

The accompanying illustration in color shows a typical specimen of the flowers and foliage. The colors are as correct as it is possible to reproduce them by this type of representation.

A detailed description of the new variety of rose follows, and to facilitate identification of the important colors described in this specification, the designations adopted by the British Horticultural Colour Charts have been followed.

This new rose belongs to the outdoor bush type and is of the so-called hybrid tea class. Its pure white flowers make it particularly desirable for cut flowers and it is a great asset to any garden.

*The Flower*

Locality where grown and observed: Montebello, California, at Temple City, California and at La Puente, California.

Flowers borne: Mainly single with stems approximately eighteen inches in length.

Number of blooms: When grown outdoors the plant produces an abundant number of flowers, there usually being about twenty-five blooms on a plant.

Continuity: Blooms continuously throughout the flowering season which normally extends from the first of April until the last of November in the coastal portion of southern California, with the maximum flowering occurring in April, May, and June, and again in September, October, and November.

Fragrance: This variety has exceptionally good fragrance for a white rose and is probably one of the most fragrant of those varieties being grown at the present time.

Bud:

*Peduncle.*—Length—length varies between 2½" to 3½". Color—usually a Kelly green.

*Before calyx breaks.*—Size—medium, usually from 9/16" to 5/8". Form—medium length, high centered and conical.

*As calyx breaks.*—Color—creamy white. Sepals—pointed; light green inside and darker green outside varying in size between 5/16" and ¾".

*As first petal opens.*—Size—approximately one and one-half inches by one and one-half inches. Color—white with base shading to a pale lemon or cream. Form—orbicular-cuneate with margin slightly reflexed. Opening—opens up normally and is not particularly affected by cold, hot, wet or dry atmospheric conditions.

Bloom:

*Size.*—Averages 3½" when fully opened.

*Petalage.*—Number of petals vary from twenty-five to thirty, arranged regularly.

*Form.*—High centered and globular at first becoming fully opened, the inner petals being somewhat smaller than the outer petals.

*Petals.*—Texture—thick and leathery with inner petals having a slightly velvety appearance and the outer petals having a satiny look. Shape—all petals are orbicular-cuneate with the edges entire and slightly reflex.

(This description of a newly opened flower was taken from observations made on a rose grown in Temple City, California, in the month of October.)

*Color.*—Petals are pure white after the flower has fully opened. This is true for all petals.

The flower has the general characteristics as hereinafter set forth:

*General color effect.*—Pure white giving the flower an outstanding appearance.

*Behavior.*—Petals drop off clean. Petals are persisent and are not inordinately affected by hot, cold, wet or dry weather.

*Flower longevity.*—Flowers have average longevity, after cutting they will usually last about five days. If flowers are left on plant in a garden they will last slightly longer.

*Reproductive organs*

Stamens: Average number of stamens varies from 45 to 55.

Filaments: Filaments are medium length, approximately ¼" long. Color—pinkish yellow.

Anthers: Anthers are medium sized and all open approximately at the same time. Color—golden yellow.

Pollen: Moderate quantity. Color—golden yellow.

Pistils: Pistils are numerous.

Styles: The styles are moderately even; average length about ¼"; average caliper and bunched.

Stigma: Not prominent.

Ovaries: Ovaries are usually enclosed in the calyx.

Hips:

*Length.*—Average length.

*Form.*—Ovoid generally, approximately ⅜" by ⅜"; slightly pear shaped.

*Color.*—Dark green outside, somewhat lighter inside.

Seeds: The seeds are of average size but do not set freely.

*The plant*

Foliage:

*Leaves.*—Compound of an average of five leaflets; normal in quantity; leathery and dull with edge serrate. Shape—ovate in shape with end acute. Size—about 1¼" in width and 1¾" in length.

Color—Parsley Green oo962/1 on upper side; Willow Green ooo862/1 on underside.

*Leaflets.*—Shape—ovoid with apex acute; margins are simply serrate. Color: mature leaves—upper side is Parsley Green oo962/1, with the lower side of the leaflet Willow Green ooo862/1; young leaves—have approximately the same color as mature leaves but have a more pronounced reddish cast.

*Type.*—Imparipinnate.

*Stipules.*—Not prominent.

Growth:

*Habit.*—Upright and well branched. Plant grows from five to six feet in height; hardy and vigorous.

*Canes.*—½″ to ¾″ in diameter after plant is established.

*Main stems.*—Some stems reach a length of 24″. Color—bright green. Prickles—approximately 3/16″ in length and widely spaced, pointing slightly downward; color—pale green; hair—none. Small prickles—none.

*Branches.*—Color—light green. Shape—predominantly vertical. Hair—none. Small prickles—none.

*New shoots.*—Color—same as mature growth but more maroon. Large prickles—scarcely noticeable. Small prickles—none.

Having described my invention, I claim:

The new and distinct variety of rose plant of the class designated as hybrid tea roses, substantially as herein shown and described, characterized particularly as to novelty by the distinctive pure white flowers borne singly on long stems, the exceptionally strong fragrance for a white rose, the medium size of the blooms and abundance of flowers throughout the growing season, the prolonged longevity of the blooms after they are cut, and its tall vigorous upright growth.

No references cited.

ABRAHAM G. STONE, *Primary Examiner.*